(12) United States Patent
Ho (10) Patent No.: US 11,707,588 B2
(45) Date of Patent: Jul. 25, 2023

(54) DETERMINING PATIENT INTERFACE DEVICE OPTIMAL HARDNESS

(71) Applicant: KONINKLIJKE PHILIPS N.V., Eindhoven (NL)

(72) Inventor: Peter Chi Fai Ho, Eindhoven (NL)

(73) Assignee: KONINKLIJKE PHILIPS N.V., Eidnhoven (NL)

( * ) Notice: Subject to any disclaimer, the term of this patent is extended or adjusted under 35 U.S.C. 154(b) by 2025 days.

(21) Appl. No.: 15/308,685

(22) PCT Filed: Apr. 15, 2015

(86) PCT No.: PCT/IB2015/052732
§ 371 (c)(1),
(2) Date: Nov. 3, 2016

(87) PCT Pub. No.: WO2015/170207
PCT Pub. Date: Nov. 12, 2015

(65) Prior Publication Data
US 2017/0182273 A1 Jun. 29, 2017

Related U.S. Application Data

(60) Provisional application No. 61/989,034, filed on May 6, 2014.

(51) Int. Cl.
*A61M 16/06* (2006.01)
*G06T 17/00* (2006.01)
*G06T 19/00* (2011.01)

(52) U.S. Cl.
CPC ......... *A61M 16/0605* (2014.02); *G06T 17/00* (2013.01); *G06T 19/00* (2013.01); *A61M 16/0622* (2014.02); *A61M 16/0683* (2013.01); *A61M 2016/0661* (2013.01); *A61M 2205/52* (2013.01); *A61M 2205/583* (2013.01); *G06T 2200/04* (2013.01); *G06T 2210/41* (2013.01)

(58) Field of Classification Search
CPC ..... A61M 16/0605; G06T 17/00; G06T 19/00
USPC .......................................................... 703/1
See application file for complete search history.

(56) References Cited

U.S. PATENT DOCUMENTS 8,634,900 B2 * 1/2014 Smith ................. A61B 5/015
382/128
2004/0263863 A1 * 12/2004 Rogers ............. A61F 13/00987
356/602

(Continued)

FOREIGN PATENT DOCUMENTS

DE 10138416 A1 2/2003
DE 10226587 A1 1/2004

(Continued)

*Primary Examiner* — Iftekhar A Khan
(74) *Attorney, Agent, or Firm* — Michael W. Haas (57) ABSTRACT

A system for determining an optimal hardness of a patient interface device includes a fit score determination unit structured to receive a 3-D model of the patient interface device and a 3-D model of a patient's face and to determine a fit score between the patient interface device and the patient's face based on the 3-D model of the patient interface device and the 3-D model of the patient's face, and a hardness determination unit structured to determine a hardness value of the patient interface device based on the determined fit score.

12 Claims, 11 Drawing Sheets

(56) References Cited

U.S. PATENT DOCUMENTS

| | | | |
|---|---|---|---|
| 2005/0199239 A1* | 9/2005 | Lang | A61M 16/0605 128/206.24 |
| 2006/0023228 A1* | 2/2006 | Geng | A61B 5/411 356/601 |
| 2006/0096598 A1* | 5/2006 | Ho | A61M 16/0616 128/206.24 |
| 2006/0235877 A1* | 10/2006 | Richard | A61M 16/06 |
| 2007/0221227 A1* | 9/2007 | Ho | A61M 16/06 128/206.24 |
| 2008/0060649 A1* | 3/2008 | Veliss | A62B 18/025 128/207.18 |
| 2008/0060652 A1* | 3/2008 | Selvarajan | A61M 16/0683 128/206.21 |
| 2009/0132371 A1* | 5/2009 | Strietzel | G06Q 30/02 705/14.46 |
| 2011/0088699 A1* | 4/2011 | Skipper | A61M 16/06 128/206.26 |
| 2011/0162654 A1* | 7/2011 | Carroll | A61M 16/06 128/206.21 |
| 2011/0174310 A1* | 7/2011 | Burz | B29C 45/4407 425/577 |
| 2011/0197341 A1* | 8/2011 | Formica | B32B 7/12 2/209.3 |
| 2011/0220112 A1* | 9/2011 | Connor | A61M 16/06 128/206.24 |
| 2012/0067349 A1* | 3/2012 | Barlow | A61M 16/0075 128/205.25 |
| 2012/0080035 A1* | 4/2012 | Guney | A61M 16/0616 128/205.25 |
| 2013/0199537 A1* | 8/2013 | Formica | A61M 16/0816 128/205.25 |
| 2013/0319422 A1* | 12/2013 | Ho | A61M 16/0605 128/206.21 |
| 2014/0150804 A1* | 6/2014 | Shalon | A61F 5/566 128/848 |
| 2014/0290663 A1* | 10/2014 | Rothermel | A61M 16/0816 128/206.24 |
| 2014/0332007 A1* | 11/2014 | Znamenskiy | B29D 99/0071 128/206.24 |
| 2015/0193650 A1* | 7/2015 | Ho | G06F 18/22 382/128 |
| 2015/0217074 A1* | 8/2015 | Wells | A61M 16/06 128/207.18 |
| 2015/0217518 A1* | 8/2015 | Chun | A61M 16/06 700/98 |
| 2015/0273170 A1* | 10/2015 | Bachelder | A61M 16/0611 264/129 |
| 2015/0290415 A1* | 10/2015 | Dunn | A61M 16/0057 128/205.25 |
| 2015/0314095 A1* | 11/2015 | Himes, Jr. | A61M 16/06 264/249 |
| 2015/0314096 A1* | 11/2015 | Chodkowski | A61M 16/06 29/428 |
| 2015/0374944 A1* | 12/2015 | Edwards | A61M 16/024 128/205.25 |
| 2016/0001029 A1* | 1/2016 | Bayer | A61M 16/0611 128/206.24 |
| 2016/0022947 A1* | 1/2016 | Heatherington | A61M 16/0825 128/205.25 |
| 2016/0078687 A1* | 3/2016 | Van Bree | G06F 3/04815 345/419 |
| 2016/0296720 A1* | 10/2016 | Henry | A61M 16/0875 |
| 2017/0128689 A1* | 5/2017 | Law | A61M 16/0683 |
| 2017/0203071 A1* | 7/2017 | Lawrenson | G06T 7/0014 |
| 2017/0239437 A1* | 8/2017 | Scheirlinck | A61M 16/0622 |
| 2018/0043122 A1* | 2/2018 | Oenning | A61M 16/0605 |
| 2018/0116863 A1* | 5/2018 | Shah | A61B 5/02055 |
| 2018/0250486 A1* | 9/2018 | Amarasinghe | A61M 16/08 |
| 2018/0272094 A1* | 9/2018 | Eves | A61M 16/0616 |
| 2018/0361096 A1* | 12/2018 | Grashow | A61M 16/0683 |
| 2019/0224436 A1* | 7/2019 | Cheng | A61M 16/065 |
| 2019/0232013 A1* | 8/2019 | Yu | A61B 5/6819 |
| 2019/0262567 A1* | 8/2019 | Davis | A61B 5/4818 |
| 2019/0290875 A1* | 9/2019 | Amarasinghe | A61M 16/0057 |

FOREIGN PATENT DOCUMENTS

| | | | |
|---|---|---|---|
| EP | 1116492 A2 | 7/2001 | |
| WO | WO2014053966 A2 | 4/2014 | |
| WO | WO-2015170207 A1 * | 11/2015 | A61M 16/0605 |

\* cited by examiner

DETERMINING PATIENT INTERFACE DEVICE OPTIMAL HARDNESS

CROSS-REFERENCE TO RELATED APPLICATIONS

This patent application claims the priority benefit under 35 U.S.C. 0 371 of international patent application No. PCT/IB2015/052732, filed Apr. 15, 2015, which claims the priority benefit under 35 U.S.C. § 119(e) of U.S. Provisional Application No. 61/989,034 filed on May 6, 2014, the contents of which are herein incorporated by reference.

BACKGROUND OF THE INVENTION

1. Field of the Invention

The present invention pertains to patient interface device hardness, and, in particular, to a system and method for determining patient interface device optimal hardness.

2. Description of the Related Art

Obstructive sleep apnea (OSA) is a condition that affects millions of people from around the world. OSA is characterized by disturbances or cessation in breathing during sleep. OSA episodes result from partial or complete blockage of airflow during sleep that lasts at least 10 seconds and often as long as 1 to 2 minutes. In a given night, people with moderate to severe apnea may experience complete or partial breathing disruptions as high as 200-500 per night. Because their sleep is constantly disrupted, they are deprived of the restorative sleep necessary for efficient functioning of body and mind. This sleep disorder has also been linked with hypertension, depression, stroke, cardiac arrhythmias, myocardial infarction and other cardiovascular disorders. OSA also causes excessive tiredness.

Non-invasive ventilation and pressure support therapies involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient.

Typically, patient interface devices include a mask shell or frame having a cushion attached to the shell that contacts the surface of the patient. The mask shell and cushion are held in place by a headgear that wraps around the head of the patient. The mask and headgear form the patient interface assembly. A typical headgear includes flexible, adjustable straps that extend from the mask to attach the mask to the patient.

Because patient interface devices are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. Additionally, an improperly fitted mask can cause red marks or pressure sores on the face of the patient.

Another concern is that an improperly fitted patient interface device can include gaps between the patient interface device and the patient that cause unwanted leakage and compromise the seal between the patient interface device and the patient. A properly fitted patient interface device should form a robust seal with the patient that does not break when the patient changes positions or when the patient interface device is subjected to external forces. While the geometry of a patient interface device is a primary factor in whether the patient interface device fits the patient well, face contacting portions of the patient interface device having a lower hardness value can more easily deform to close gaps between the patient interface device and the patient. However, it is not desirable for the patient interface device to deform more than necessary to close gaps and create a seal with the patient's face.

SUMMARY OF THE INVENTION

In one embodiment, a system for determining an optimal hardness of a patient interface device includes a fit score determination unit structured to receive a 3-D model of the patient interface device and a 3-D model of a patient's face and to determine a fit score between the patient interface device and the patient's face based on the 3-D model of the patient interface device and the 3-D model of the patient's face, and a hardness determination unit structured to determine a hardness value of the patient interface device based on the determined fit score.

In another embodiment, a method for determining an optimal hardness of a patient interface device includes receiving a 3-D model of the patient interface device, receiving a 3-D model of a patient's face, determining a fit score between the patient interface device and the patient's face based on the 3-D model of the patient interface device and the 3-D model of the patient's face, and determining a hardness value of the patient interface device based on the determined fit score.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As used herein, the word "hardness" in the context of patient interface devices means the resistance of a face contacting portion of the patient interface device to deformation. Hardness refers to the combination of the actual hardness and effective hardness of the face contacting portion of the patient interface device. The actual hardness of the face contacting portion of the patient interface device may be determined, without limitation, by the materials used in the face contacting portion of the patient interface device. The effective hardness of the face contacting portion of the patient interface device may be determined by, without limitation, underlying support mechanisms such as support walls, ribs, or gel supports.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
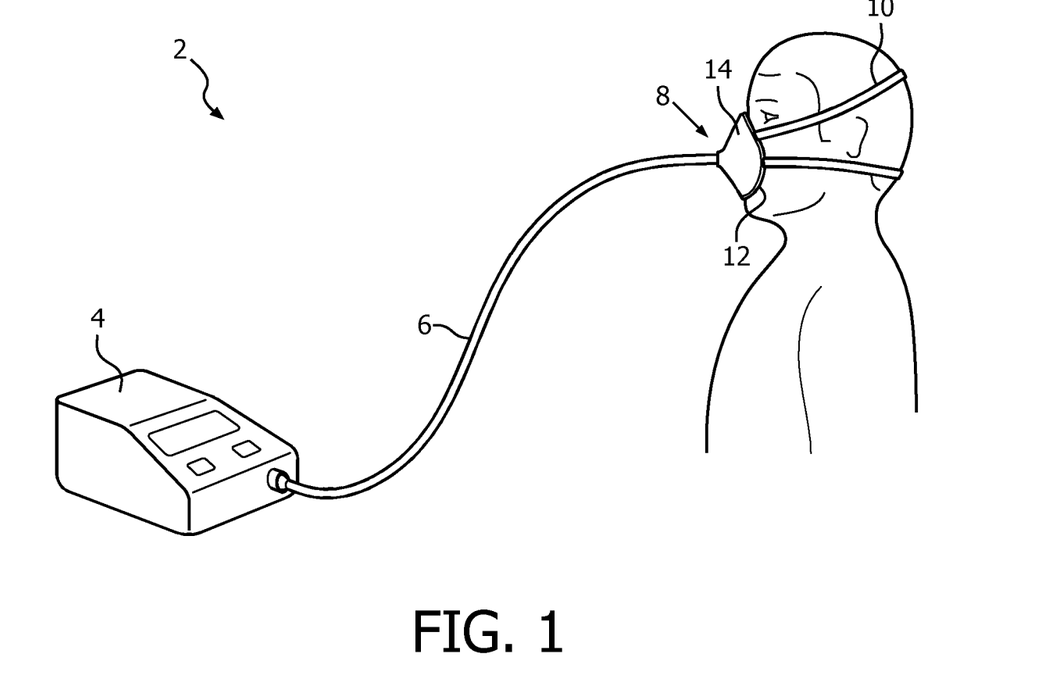
FIG. 1 is a schematic/isometric view of a system adapted to provide a regimen of respiratory therapy to a patient according to one exemplary embodiment of the disclosed concept.

A system 2 adapted to provide a regimen of respiratory therapy to a patient is generally shown in FIG. 1. System 2 includes a pressure/flow generator 4, a delivery conduit circuit 6, a patient interface device 8 and a headgear 10 for securing patient interface device 8 to the head of a patient (not numbered). Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8. Delivery conduit 6 and patient interface device 8 are often collectively referred to as a patient circuit.

A BiPAP® device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. For present purposes, pressure/flow generating device 4 is also referred to as a gas flow generating device, because flow results when a pressure gradient is generated. The present invention contemplates that pressure/flow generating device 4 is any conventional system for delivering a flow of gas to an airway of a patient or for elevating a pressure of gas at an airway of the patient, including the pressure support systems summarized above and non-invasive ventilation systems.

In the illustrated example system 2 of FIG. 1, patient interface device 8 is depicted as a nasal/oral mask which includes a patient sealing assembly in the form of a cushion 12 coupled to a generally rigid frame member of faceplate 14 which may be coupled to conduit 6 either directly or indirectly via any suitable coupling mechanism.

Figure 2:
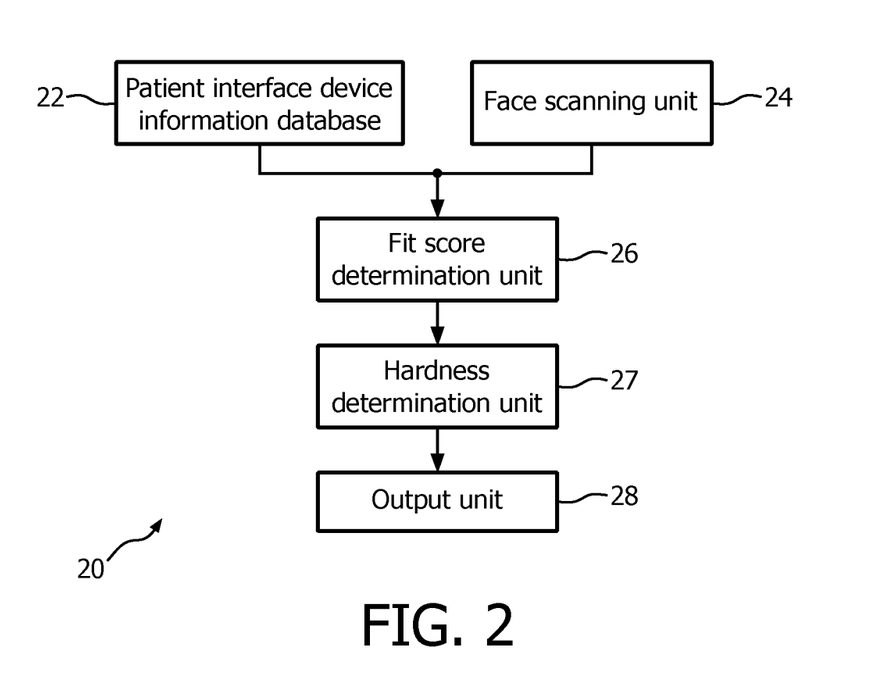
FIG. 2 is a schematic view of a system for determining a hardness value for a patient interface device in accordance with exemplary embodiments of the disclosed concept.

FIG. 2 illustrates a system 20 for determining the optimal hardness of a patient interface device. The determined hardness is a desired or optimal hardness, not the actual hardness of the patient interface device. System 20 includes a patient interface device information database 22, a face scanning unit 24, a fit score determination unit 26, a hardness determination unit 27, and an output unit 28.

Patient interface device information database 22 is structured to store 3-D models of one or more patient interface devices. The 3-D models of the patient interface devices do not need to include the entire 3-D patient interface device, but rather may be limited to the portions of the patient interface device that are intended to contact the patients face such as a cushion or a face contacting side of a cushion. Patient interface device information database may be any medium suitable for storing data such as, without limitation, a hard drive or a memory card. The geometric information of the patient interface devices may be obtained in a suitable manner such as, without limitation, using a 3-D optical scanner or any other suitable device for creating a 3-D model of the patient interface devices. Patient interface device information database 22 is structured to output the geometric information of the patient interface devices to fit score determination unit 26.

Face scanning unit 24 is structured to scan a patient's face and to create a 3-D model of the patient's face. Face scanning unit 24 may be, without limitation, a 3-D optical scanner, a camera, a push-pin array, or any other device suitable for creating a 3-D model of the patient's face. Face scanning unit 24 is structured to output the 3-D model of the patient's face to fit score determination unit 26.

Fit score determination unit 26 is structured to determine a fit between the patient and a patient interface device by using the 3-D models of the patient's face and the patient interface device. Fit score determination unit 26 may be embodied in or include a microprocessor, a microcontroller, or any other suitable processor. Fit score determination unit 26 fits the 3-D model of the patient interface device to the 3-D model of the patient's face and determines how well the geometries of the patient interface device and the patient's face fit together. For example, when the geometry of a face contacting portion of the patient interface device and the patient's face match such that there are little or no gaps between them, then the patient interface device would receive a fit score indicating a good fit. Whereas, when the geometries of the face contacting portion of the patient interface device and the patient's face do not match well such that there are large gaps between the two, then the patient interface device will receive a fit score indicating a poor fit. An example of a fit score determination that can be performed by fit score determination unit 26 will now be described in more detail with respect to FIG. 3.

Figure 3:
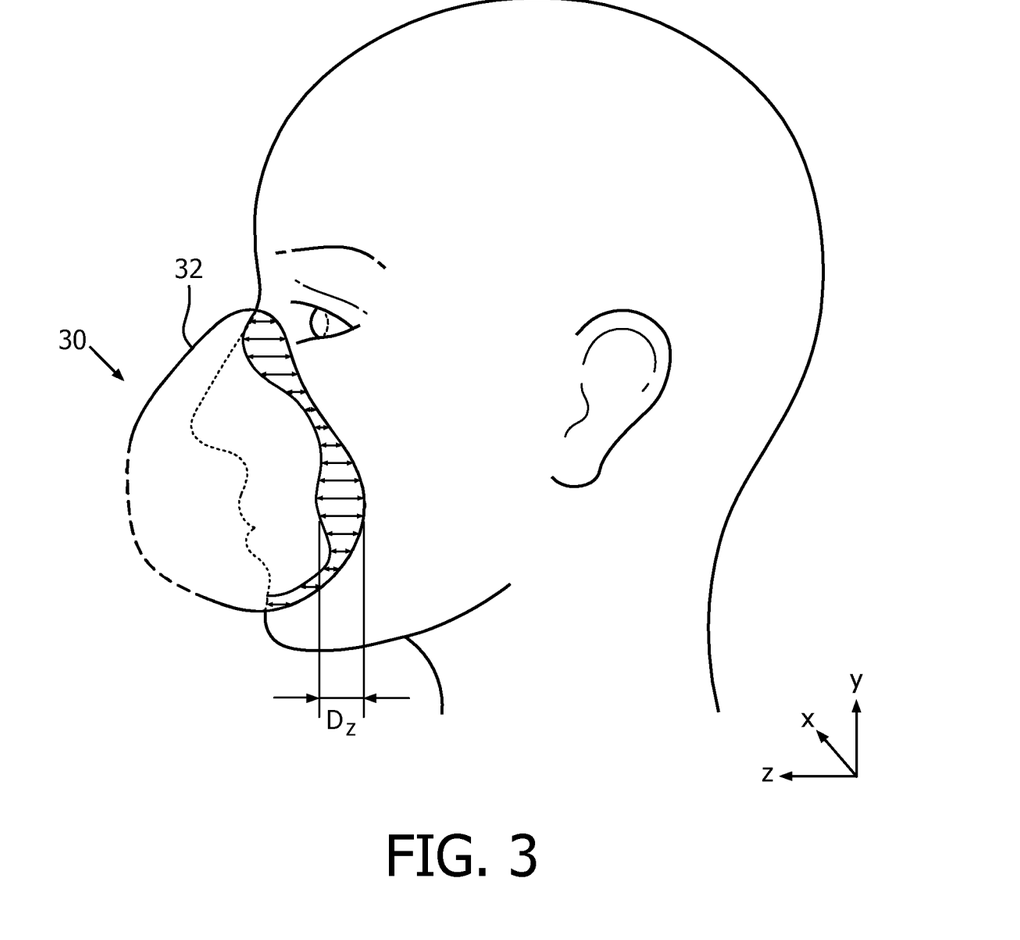
FIG. 3 is a view of a Dz between a cushion and a patient's face in accordance with exemplary embodiments of the disclosed concept.

Referring to FIG. 3, a portion of patient interface device 30 is shown fitted to a patient's face is shown. Patient interface device 30 includes a cushion 32 which includes a patient contacting portion that is structured to be in direct contact with the patient's face when patient interface device 30 is fitted to the patient. As shown in FIG. 3, the geometries of the patient contacting portion of cushion 32 and the patient's face do not match exactly. Rather, there is a gap of varying width in the z-direction which is referred to as a delta-z or Dz between the patient interface device and the patient's face. Although not shown in FIG. 3, gaps in the y-direction and x-direction can also be determined and are referred to as Dy and Dx.

To determine the fit score between patient interface device 30 and the patient's face Dx, Dy, and Dz can be used to determine how well the geometries of patient interface device 30 and the patient's face match. For example, the root mean squares (RMS) for Dx, Dy, and Dz can be calculated. Lower RMS values for Dx, Dy, and Dz indicate a better fit between patient interface device 30 and the patient's face, and as the RMS values for Dx, Dy, and Dz increase, the fit becomes worse. In some example embodiments the RMS values typically vary between 0.5 and 5.5, with 0.5 being a unit to divide the fit between categories from 1 to 10, with category 1 corresponding to the best fit score of RMS values equal to or less than 0.5.

Figure 4:
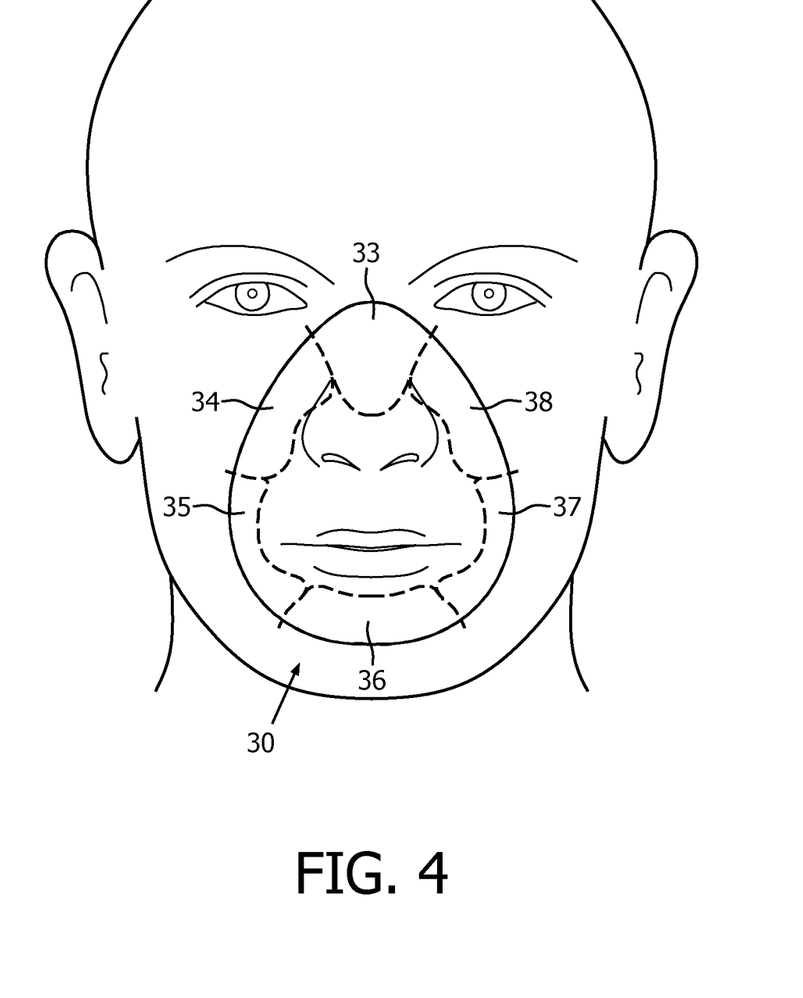
FIG. 4 is a view of a cushion including multiple segments in accordance with exemplary embodiments of the disclosed concept.

Although an example using RMS values of Dx, Dy, and Dz is described herein, it is contemplated that the method for determining the fit score between patient interface device 30 and the patient's face may be modified in any suitable manner. For example and without limitation, Dx, Dy, and Dz values may each have different weightings when determining the fit score. In another example, only the Dz value is used to determine the fit score, which can reduce the number of calculations to determine the fit score. In yet another example, fit scores are determined for different segments of patient interface device 32. For example, referring to FIG. 4, patient interface device 30 is divided into six face contacting portions 33,34,35,36,37,38. Fit scores may be individually determined for each of the six face contacting portions 33,34,35,36,37,38.

Referring back to FIG. 2, it is contemplated that the fit score determinations described above with reference to FIGS. 3 and 4 may be performed by fit score determination unit 26 by using 3-D models of a patient device and the patient's face. When fit score determination unit 26 determines the fit score, or fit scores in the case that multiple fit scores are determined, the fit score is output to hardness determination unit 27.

Hardness determination unit 27 is structured to use the fit score received from fit score determination unit 26 to determine a hardness for the patient interface device. Hardness determination unit 27 may be embodied in or include a microprocessor, a microcontroller, or any other suitable processor. When a patient interface device is fitted to a patient's face, there will be deformation of both the face contacting portions of the patient interface device and the patient's face, which have the effect of closing any gaps and creating a seal between the patient interface device and the patient's face. It is desirable to have little deformation of the patient interface device, and when the patient interface device fits the patient's face well, little or no deformation is required from the patient interface device to create a suitable seal. However, when the patient interface device does not fit the patient's face as well, more deformation from the patient interface device helps to create the seal. The hardness of the face contacting portions of the patient interface device, such as the cushion, determine how easily the patient interface device will deform.

When the fit score indicates a good fit between the patient interface device and the patient's face, hardness determination unit 27 outputs a higher hardness value for the patient interface device. When the fit score indicates a poor fit between the patient interface device and the patient's face, hardness determination unit 27 outputs a lower hardness value for the patient interface device. It is contemplated that the resolution of fit scores and hardness values may be modified or customized as desired by the user. For example, fit scores ranging from categories 1-10 were described in an example above. In this example, corresponding hardness values may start at a predetermined base hardness value for category 1 (the best fit score). The hardness value is then reduced by 5%, or another predetermined percentage, for each subsequent category. Thus, category 2 would have a corresponding hardness value of 5% less than the base hardness value and so on to category 10 which would have a corresponding hardness value of 50% less than the base hardness value. In other words, the hardness values corresponding to the second best fit score through the worst fit score are determined by decrementing the predetermined base hardness value by a predetermined percentage.

While this is just one example of corresponding fit scores and hardness values, it is contemplated that the number of fit scores and their corresponding hardness values may be determined in any suitable manner. As another example, hardness values may be termed "SOFT", "MEDIUM", and "FIRM", with each of these categories having a predetermined hardness value for the selected patient interface device. A fit score or range of fit scores may correspond to each of these hardness categories.

In some exemplary embodiments, a specific hardness value for a single patient and patient interface device can be selected based on the fit score for that patient and patient interface device. For example and without limitation, custom criteria can be used to derive the hardness value from the fit score and the patient interface device can be created or modified to have the derived hardness value.

In addition to determining a single hardness value corresponding to the patient interface device, it is also contemplated that hardness determination unit 27 may determine a plurality of different hardness values, each corresponding to different segments of the patient interface device. For example, as described above with reference to FIG. 4, individual fit scores could be determined for different segments of the patient interface device. Similarly, individual hardness values may be determined for different segments of the patient interface device. Once hardness determination unit 27 determines the one or more hardness values corresponding to the patient interface device, the hardness values are output to output unit 28.

Output unit 28 is structured to output the hardness values it receives to a user such as a caregiver, patient interface device manufacturer, or any other entity that has use for the hardness values. Output unit 28 may be any suitable device for outputting the hardness values in a useful manner such as, without limitation, a display device. It is also contemplated that the fit scores may be output to the output unit 28 if desired. The hardness values can then be used to select, customize, or create a patient interface device to have the desired hardness. Some examples of manners in which the hardness of face contacting portions of patient interface devices are controlled will be described hereinafter with respect to FIGS. 5-11.

Figure 5A:
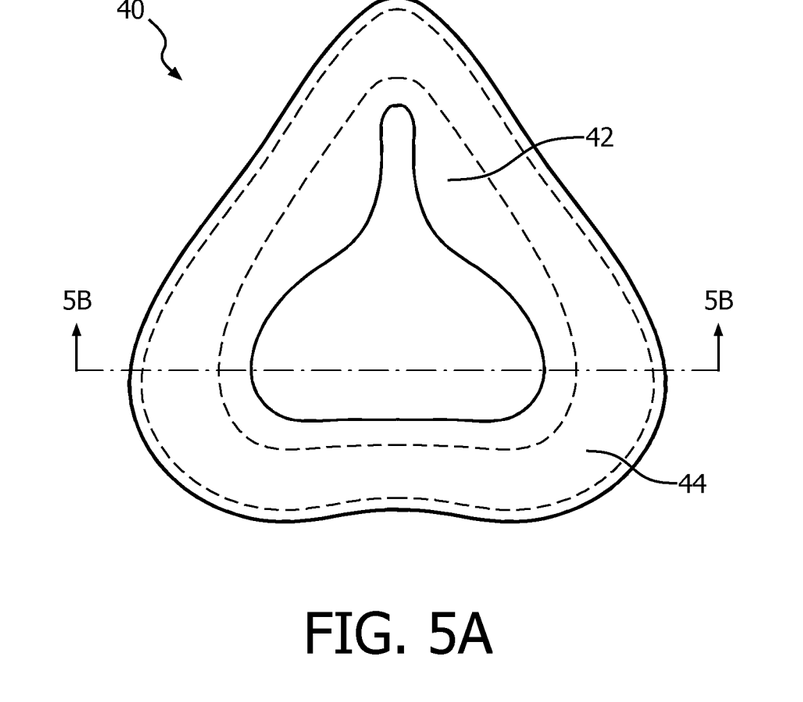
FIG. 5A is a view of a face contacting side of a cushion in accordance with an exemplary embodiment of the disclosed concept.
Figure 5B:
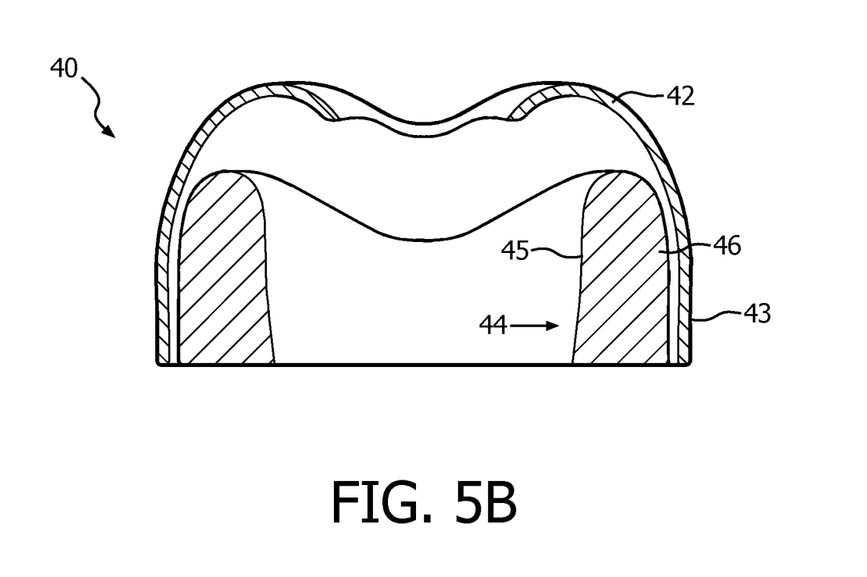
FIG. 5B is a cross-sectional view of the cushion of FIG. 5A.

FIG. 5A is a view of a face contacting side of a cushion 40 in accordance with an example embodiment of the disclosed concept, and FIG. 5B is a cross-sectional view of cushion 40. Cushion 40 includes a flap 42 that is structured to contact a patient's face when cushion 40 is fitted to the patient's face and a support wall 43 that is structured to support flap 42. Flap 42 and support wall 43 may be made of any suitable elastic material such as, without limitation, silicone, TPE (thermoplastic elastomer), or polyurethane. Cushion 40 also includes a filled portion 44 which provides further support for flap 42. Filled portion 44 includes a membrane 45 which encloses an interior area which is filled with a filler material 46. Filler material 46 may include any deformable materials such as, without limitation, silicone, silicone gel, polyurethane gel, closed cell foam, open cell foam, or TPE.

The hardness of cushion 40 may be controlled in a number of ways. For example, the material used for flap 42, support wall 43, and/or filler material 46 may be selected to achieve a desired hardness. In one example, filler material 46 includes a mixture of Isocyanate (NCO) and Polyol (OH). The ratio of NCO and OH affects its hardness, and therefore can be used to manipulate the hardness of cushion 40. Similarly, when two part silicone is used as filler material 46, the ratio of the two parts of silicone affects hardness, and therefore can also be used to manipulate the hardness of cushion 40. Manipulating the ratio of materials used in filler material 46 or other parts of cushion 40 can precisely control the hardness of cushion 40 and is particularly suitable for use when precise control of the hardness is needed, such as in exemplary embodiments where a particular hardness value is derived from the fit score for a particular patient and patient interface device.

The hardness of cushion 40 may also be manipulated by modifying the thickness of flap 42 and/or support wall 43, or by modifying the size and/or shape of filled portion 44. Additionally, for example and without limitation, when open cell or closed cell foam is used as filler material 46, the hardness or firmness of the foam can be controlled by controlling the density and/or size of the cells.

Figure 6A:
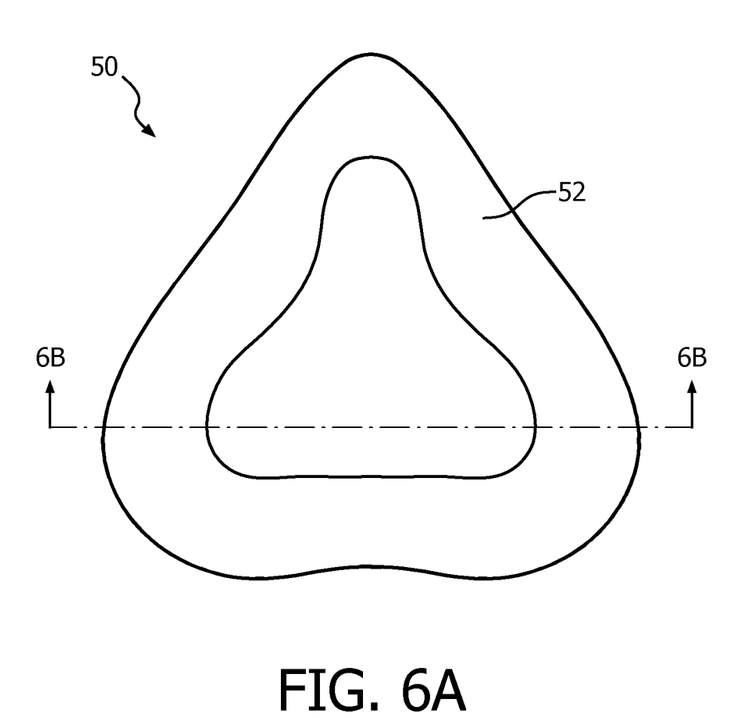
FIG. 6A is a view of a face contacting side of a cushion in accordance with another exemplary embodiment of the disclosed concept.
Figure 6B:
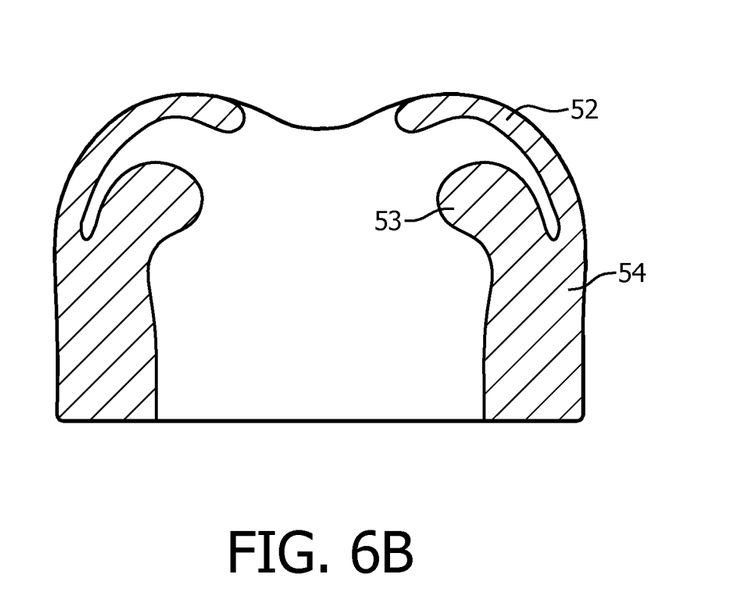
FIG. 6B is a cross-sectional view of the cushion of FIG. 6A.

FIG. 6A is a view of a face contacting side of a cushion 50 in accordance with another example embodiment of the disclosed concept, and FIG. 6B is a cross-sectional view of cushion 50. Cushion 50 includes an outer flap 52 structured to contact the patient's face. Cushion 50 also includes an inner flap 53 disposed behind outer flap 53. Cushion 50 further includes support wall 54 which supports outer and inner flaps 52,53.

The hardness of cushion 50 may be controlled by changing the material of outer flap 52, inner flap 53, and/or support wall 54. Outer flap 52, inner flap 53, and support wall 54 may be made of any suitable elastic material such as, without limitation, silicone, TPE (thermoplastic elastomer), or polyurethane. The hardness of cushion 50 may also be controlled by changing the thickness of outer flap 52, inner flap 53, and/or support wall 54.

Figure 7A:
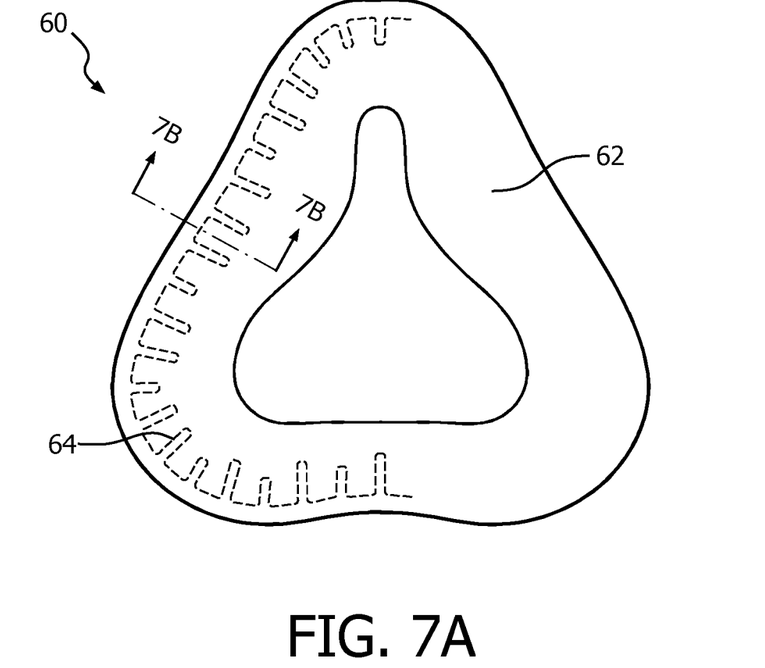
FIG. 7A is a view of a face contacting side of a cushion in accordance with another exemplary embodiment of the disclosed concept.
Figure 7B:
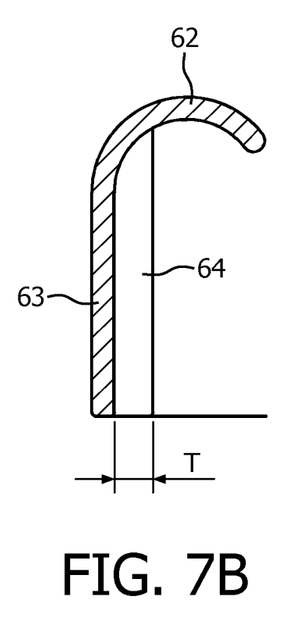
FIGS. 7B, 7C, and 7D are cross-sectional views of the cushion of FIG. 7A.
Figure 7C:
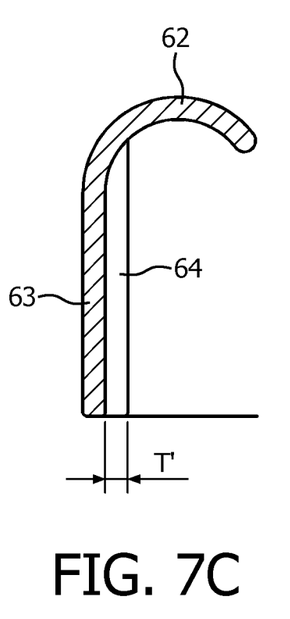
Figure 7D:
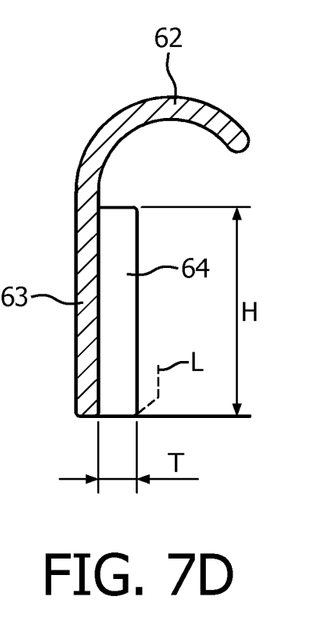

FIG. 7A is a view of a face contacting side of a cushion 60 in accordance with another example embodiment of the disclosed concept, and FIGS. 7B, 7C, and 7D are cross-sectional views of cushion 60 showing different ribs 64 included in cushion 60. Cushion 60 includes a flap 62 structured to contact the patient's face. Cushion 60 also includes a support wall 63 which provides support for flap 63. Cushion 60 further includes ribs 64 which provide further support for flap 62.

The hardness of cushion 60 may be controlled by changing the material of flap 62, support wall 63, and/or ribs 64. Flap 62, support wall 63, and ribs 64 may be made of any suitable elastic material such as, without limitation, silicone, TPE (thermoplastic elastomer), or polyurethane. The hardness of cushion 60 may also be controlled by changing the thickness of flap 62 and/or support wall 63.

The hardness of cushion 60 may further be controlled by changing the number of ribs 64 or the dimensions of ribs 64. Ribs 64 in this embodiment are discrete elements that extends away from an inner surface of support wall 63. Ribs 64 have a length L, height H, and thickness T. The length of rib 64 is the distance rib 64 extends along support wall 63. The height of rib 64 is the distance rib 64 extends up support wall 63. The thickness of rib 64 is the distance rib 64 extends away from support wall 63. FIG. 7D illustrates how the length L, height H, and thickness T of rib 64 are measured. Reducing the thickness T of rib 64, as is shown in FIG. 7B with rib 64 having a thickness T and FIG. 7C with rib 64 having a reduced thickness T', reduces the hardness of cushion 60 in the area of the selected rib 64. Similarly, reducing the height H or length L of ribs 64 reduces the hardness of cushion 60 in the area of the selected rib 64. Furthermore, reducing the number of ribs 64 in an area reduces the hardness of cushion 60 in the area. As such, the overall hardness of cushion 60, or the hardness of selected areas of cushion 60, may be controlled by changing the number or dimensions of ribs 64.

Figure 8A:
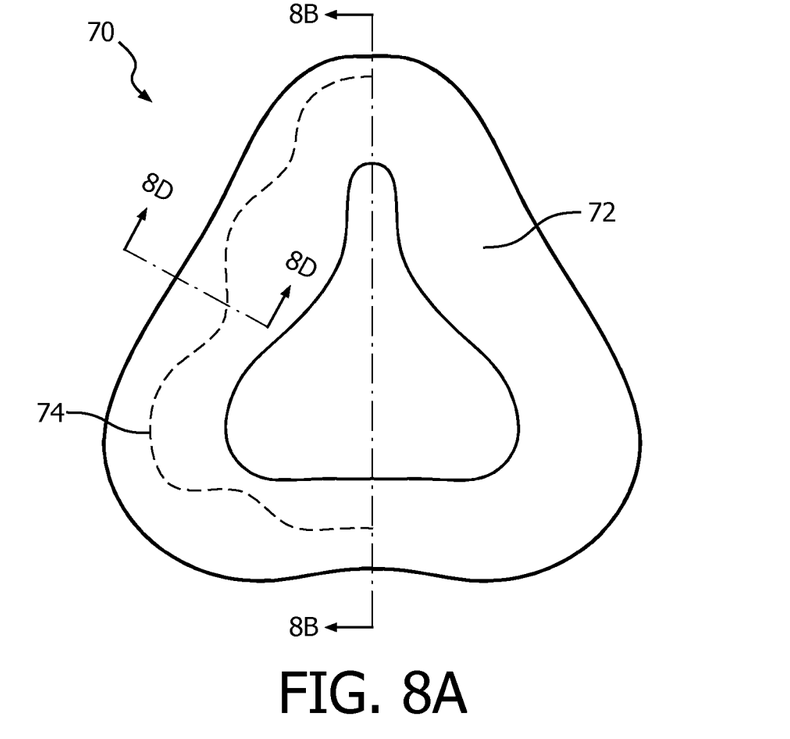
FIG. 8A is a view of a face contacting side of a cushion in accordance with another exemplary embodiment of the disclosed concept.
Figure 8B:
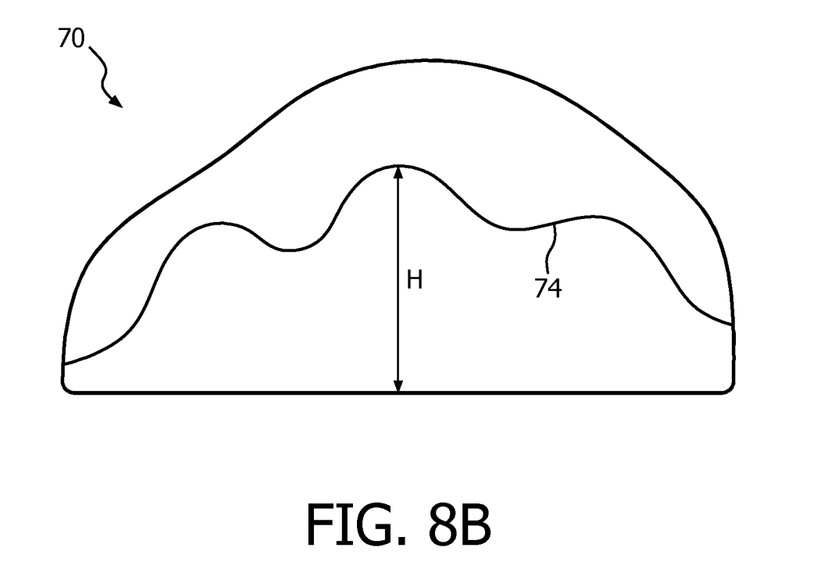
FIG. 8B is a cross-sectional view of the cushion of FIG. 8A.
Figure 8C:
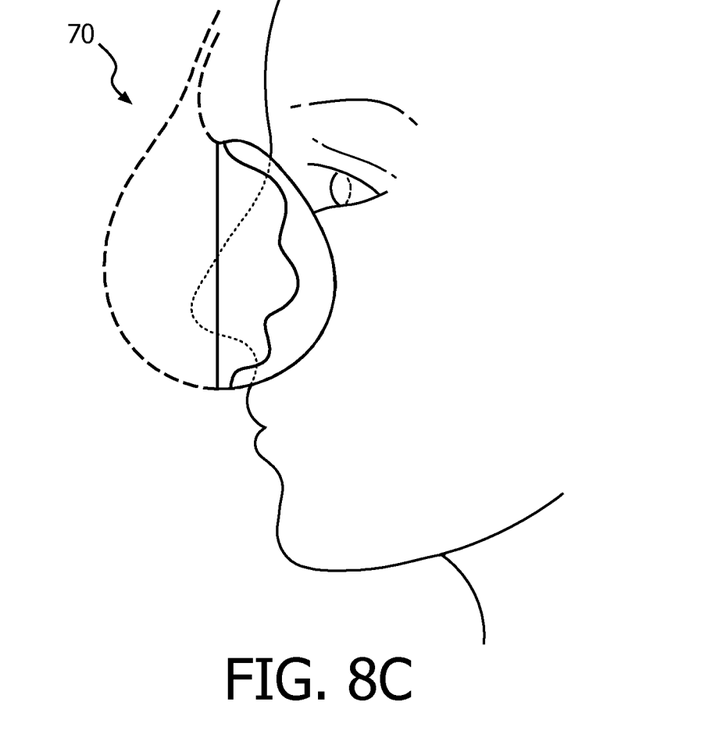
FIG. 8C is a view of the cushion of FIG. 8A fitted to a patient's face.
Figure 8D:
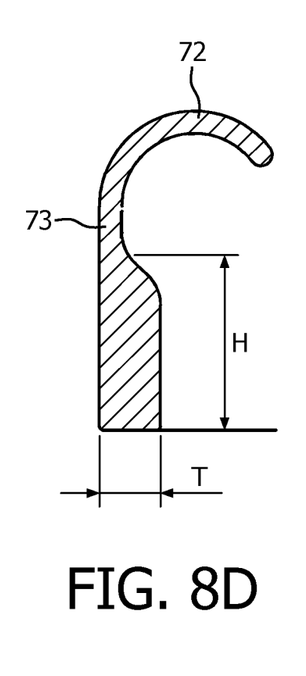
FIGS. 8D, 8E, and 8F are cross-sectional views of the cushion of FIG. 8A.
Figure 8E:
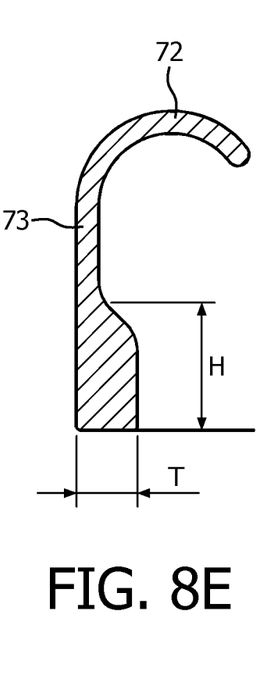
Figure 8F:
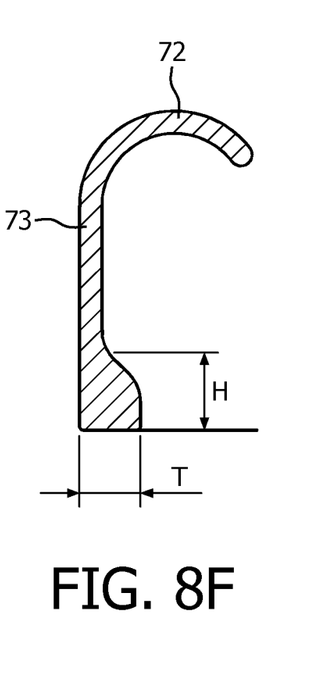

FIG. 8A is a view of a face contacting side of a cushion 70 in accordance with another example embodiment of the disclosed concept. FIG. 8B is a cross-sectional view of cushion 70 taken along section line 8B shown in FIG. 8A. FIG. 8C is a view of cushion 70 fitted to a patient's face. FIGS. 8D, 8E, and 8F are cross-sectional views of cushion 70 showing ribs 74.

Cushion 70 includes a flap 73 structured to contact the patient's face. Cushion 70 also includes a support wall 73 to provide support to flap 72. Cushion further includes rib structure 74 that provides further support to flap 72. Rib structure 74 is a continuous structure that extends from an inner surface of support wall 73 at varying thicknesses T and heights H. Unlike ribs 64 of FIGS. 7A, 7B, 7C, and 7D, which are discrete structures each having a defined length L, rib structure 74 is continuous and smoothly transitions to different thicknesses T and heights H.

The hardness of cushion 70 may be controlled by changing the material of flap 72, support wall 73, and/or rib structure 74. Flap 72, support wall 73, and rib structure 74 may be made of any suitable elastic material such as, without limitation, silicone, TPE (thermoplastic elastomer), or polyurethane. The hardness of cushion 70 may also be controlled by changing the thickness of flap 72 and/or support wall 73.

The hardness of cushion 70 may further be controlled by changing the thickness T and/or height H of areas of rib structure 74. Increasing the thickness T in an area of rib structure 74 will increase the hardness of cushion 70 in that area. Similarly, increases the height H of rib structure 74 will increase the hardness of cushion 70 in that area. Controlling the thicknesses T and heights H of areas of rib structure 74 of cushion 70 can thus be used to control the overall hardness of cushion 70 or to control hardness in specific areas of cushion 70 if it is desired to have different areas of cushion 70 have different hardness.

Figure 9:
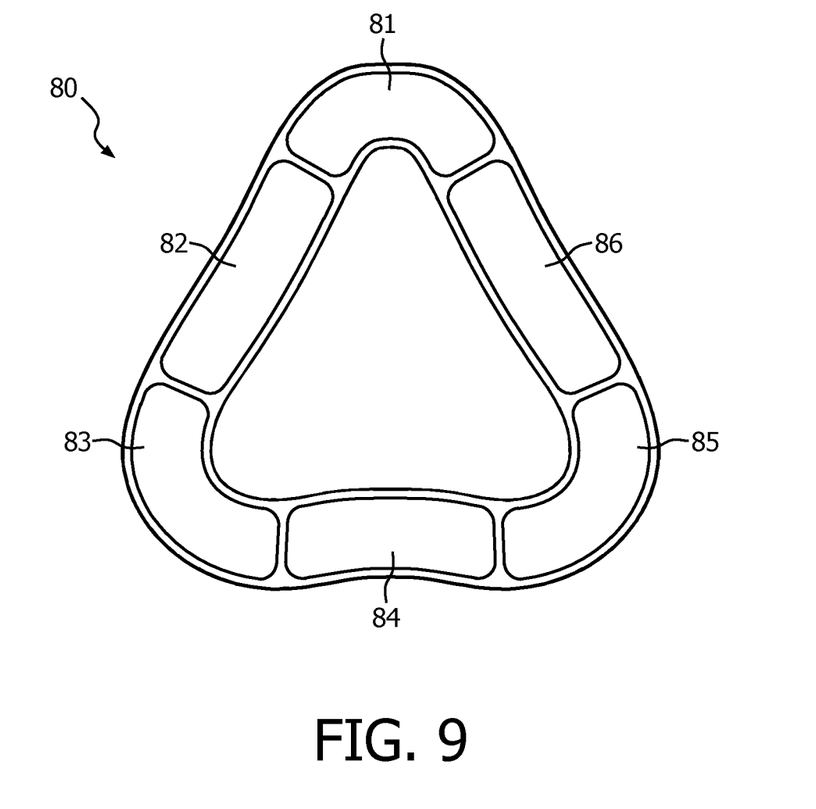
FIG. 9 is a view of a face contacting side of a cushion including multiple segments in accordance with an exemplary embodiment of the disclosed concept.

FIG. 9 illustrates a face contacting side of a cushion 80 in accordance with another example embodiment of the disclosed concept. Cushion 80 includes six filled portions 81,82,83,84,85,86. Each filled portion 81,82,83,84,85,86 corresponds to an area of the face contacting side of cushion 80. Filled portions 81,82,83,84,85,86 each include filler material that may include any deformable materials such as, without limitation, silicone, silicone gel, polyurethane gel, closed cell foam, open cell foam, or TPE.

The hardness of cushion 80 or the hardness of selected areas of cushion 80 may be controlled by using different materials in filled portions 81,82,83,84,85,86. A different material or different mixture of materials may be used for each individual filled portion 81,82,83,84,85,86 in order to provide an individual hardness for each corresponding area of cushion 80. In one example, filler portions 81,82,83,84, 85,86 each include a mixture of Isocyanate (NCO) and Polyol (OH). The ratio of NCO and OH affects its hardness, and therefore can be used to manipulate the hardness individual hardness of each filled portion 81,82,83,84,85,86.

Figure 10A:
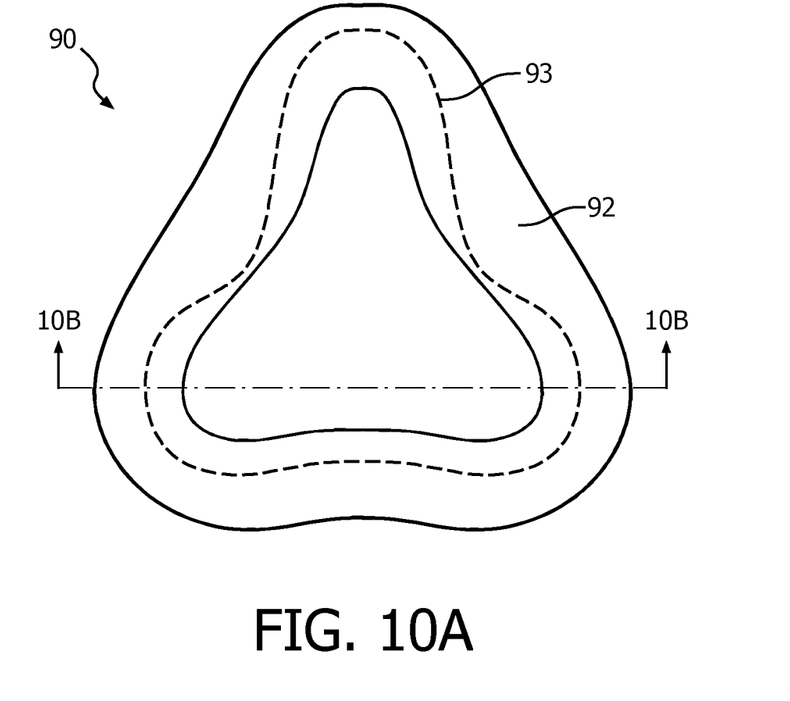
FIG. 10A is a view of a face contacting side of a cushion in accordance with an exemplary embodiment of the disclosed concept.
Figure 10B:
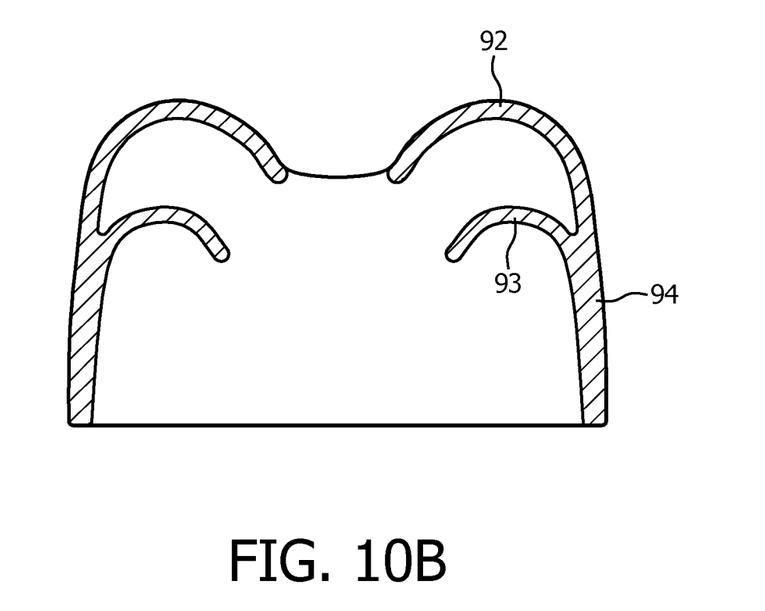
FIG. 10B is a cross-sectional view of the cushion of FIG. 10A.

FIG. 10A illustrates a face contacting side of a cushion 90 in accordance with another example embodiment of the disclosed concept, and FIG. 10B is a cross-section of cushion 90. Cushion 90 includes an outer flap 92 structured to contact the patient's face. Cushion 90 also includes an inner flap 93 disposed behind outer flap 92. Cushion 90 further includes support wall 94 structured to support outer flap 92 and inner flap 93.

The hardness of cushion 90 may be controlled by controlling the materials or mixture of materials used in outer flap 92, inner flap 93, and/or support wall 94. Outer flap 92, inner flap 93, and support wall 94 may be made of any suitable elastic material such as, without limitation, silicone, TPE (thermoplastic elastomer), or polyurethane. The hardness of cushion 90 may also be controlled by controlling thicknesses of outer flap 92, inner flap 93, and/or support wall 94.

It is contemplated that any of cushions 40, 50, 60, 70, 80, and 90 may be employed in a patient interface device, such as patient interface device 8 shown in FIG. 1. Further, it is contemplated that hardness values determined by hardness determination unit 27 of FIG. 2 may be used to select, customize, or create any of cushions 40, 50, 60, 70, 80, and 90 to have hardness in accordance with the determined hardness values.

Figure 11:
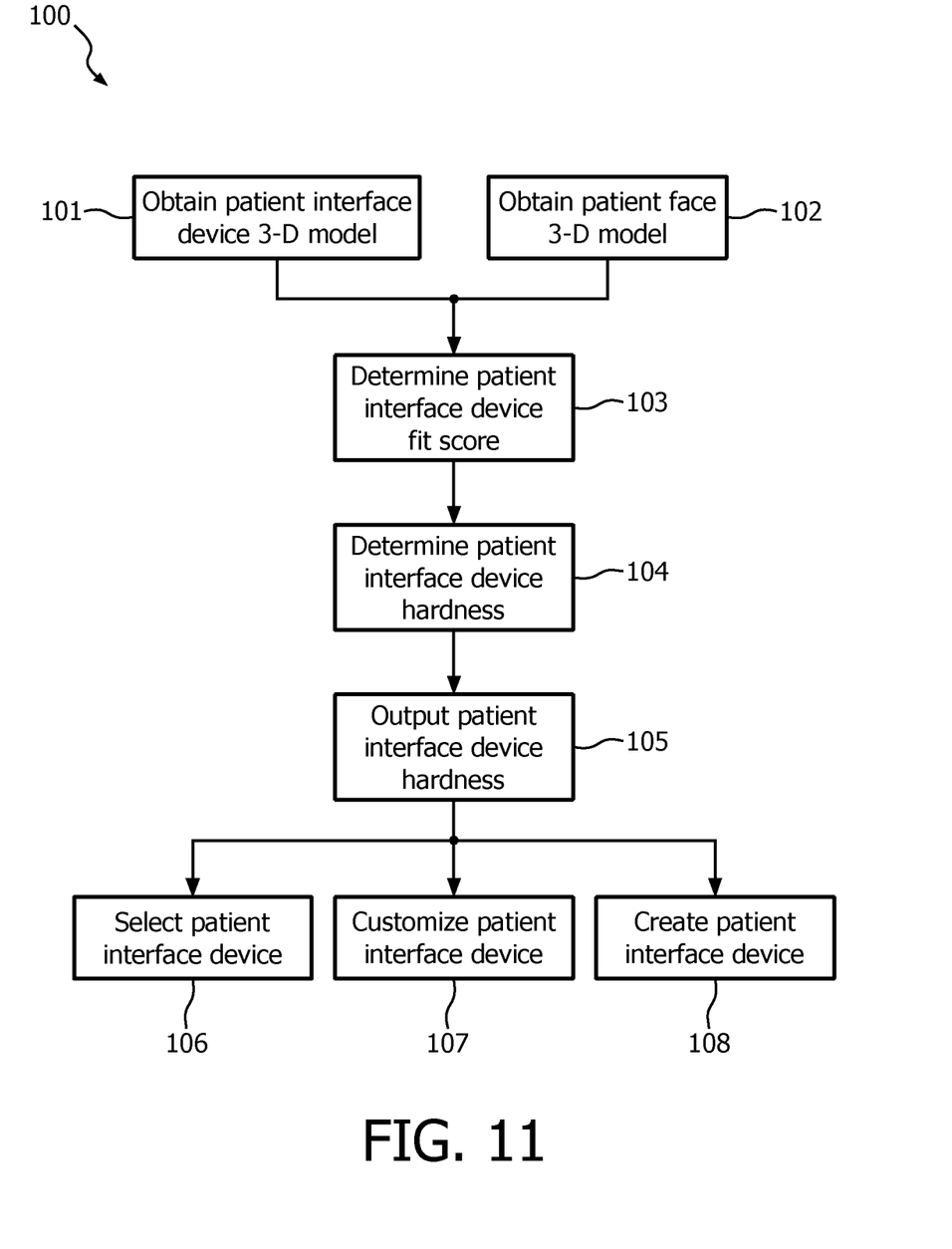
FIG. 11 is a flow chart illustrating a method of determining the hardness of a patient interface device.

FIG. 11 illustrates a method of determining patient interface device hardness 100 in accordance with embodiments of the disclosed concept. At 101, a 3-D model of a patient interface device is obtained. The 3-D model may be obtained, for example, from patient interface device information database of FIG. 2. At 102, a 3-D model of a patient's face is obtained. The 3-D model of the patient's face may be obtained, for example, by face scanning unit 24 of FIG. 2.

At 103, the fit score between the patient interface device and the patient's face is determined using the 3-D models of the patient interface device and the 3-D model of the patient's face. The fit score may be determined using any suitable method such as, without limitation, any of the methods previously described herein with respect to FIGS. 2-4. The fit score may be determined using, for example, fit score determination unit 26 of FIG. 2. At 104, the hardness value for the patient interface device is determined. The hardness value may be determined using any suitable method such as, without limitation, any of the methods previously described herein with respect to FIGS. 2-4. The hardness value may be determined using, for example, hardness determination unit 27 of FIG. 2.

At 105, the determined patient interface device hardness value is output. The determined patient interface device hardness value may be output in any suitable manner to a user such as, without limitation, a caregiver, a manufacturer, or any other entity that may desire to use the determined hardness value. The determined hardness value may be output by, without limitation, output unit 28 of FIG. 2.

After the determined hardness value is output at 105, an existing patient interface device with the desired hardness may be selected at 106, an existing patient interface device may be customized to have the desired hardness at 107, or a patient interface device having the desired hardness may be created at 108. It is selected that any of cushions 40, 50, 60, 70, 80, or 90 may be selected, customized, or created to obtain the desired hardness by modifying their characteristics effective to change their hardness, as previously described herein with reference to FIGS. 5A-10B. It is further contemplated that any of cushions 40, 50, 60, 70, 80, or 90 may then be employed in a patient interface device and provided to the patient.

It can be appreciated that the present invention provides a mechanism for a patient interface device that improves upon existing devices to, for example, determines the optimal hardness for patient interface devices.

Although some methods of controlling hardness of cushions have been described herein, the disclosed concept is not limited to the described methods. It is contemplated that any known methods of controlling the hardness of cushions may employed without departing from the scope of the disclosed concept. Furthermore, although some cushions and patient interface devices have been described herein, it is contemplated that the disclosed concept is not limited thereto. Rather, it is contemplated that the disclosed concept is applicable to any suitable patient interface device and/or cushion.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method for determining an optimal hardness of a patient interface device, the method comprising:
   receiving a 3-D model of the patient interface device;
   receiving a 3-D model of a patient's face;
   determining a fit score between the patient interface device and the patient's face based on the 3-D model of the patient interface device and the 3-D model of the patient's face;
   determining a hardness value of the patient interface device based on the determined fit score;
   customizing a patient interface device based on the determined hardness value or creating a patient interface device based on the determined hardness value;
   wherein the patient interface device includes a filled portion including filler material; and
   wherein customizing or creating the patient interface device includes selecting materials for the filler material based on the determined hardness value.

2. The method of claim 1, wherein the fit score is selected from a number of fit scores arranged sequentially from a best fit score to a worst fit score; wherein a hardness value corresponding to the best fit score is a predetermined value; and wherein the hardness values corresponding to a second best fit score to the worst fit score are determined by decrementing the predetermined value by a predetermined percentage.

3. The method of claim 1, wherein the fit score is selected from a number of fit scores; wherein the hardness value is selected from a number of predetermined hardness values; and wherein one fit score or a range of fit scores corresponds to each predetermined hardness value.

4. The method of claim 1, wherein determining the fit score includes determining a plurality of fit scores, each fit score corresponding to an individual area of the patient interface device; and wherein determining the hardness includes determining a plurality of hardness values based on the determined plurality of fit scores, each hardness value corresponding to an individual area of the patient interface device.

5. The method of claim 1, further comprising storing the 3-D model of the patient interface device in a patient interface device information database.

6. The method of claim 1, further comprising creating the 3-D model of the patient's face.

7. The method of claim 1, further comprising outputting the determined hardness value to a user.

8. The method of claim 1, further comprising selecting an existing patient interface device based on the determined hardness value.

9. A method for determining an optimal hardness of a patient interface device, the method comprising:
   receiving a 3-D model of the patient interface device;
   receiving a 3-D model of a patient's face;
   determining a fit score between the patient interface device and the patient's face based on the 3-D model of the patient interface device and the 3-D model of the patient's face;
   determining a hardness value of the patient interface device based on the determined fit score;
   customizing a patient interface device based on the determined hardness value or creating a patient interface device based on the determined hardness value,
   wherein the patient interface device includes at least one flap and a support wall; and
   wherein customizing or creating the patient interface device includes at least one of selecting materials for the at least one flap and/or the support wall and selecting the thickness of the at least one flap and/or the support wall based on the determined hardness value.

10. A method for determining an optimal hardness of a patient interface device, the method comprising:
    receiving a 3-D model of the patient interface device;
    receiving a 3-D model of a patient's face;
    determining a fit score between the patient interface device and the patient's face based on the 3-D model of the patient interface device and the 3-D model of the patient's face; and
    determining a hardness value of the patient interface device based on the determined fit score;
    customizing a patient interface device based on the determined hardness value or creating a patient interface device based on the determined hardness value,
    wherein the patient interface device includes a plurality of discrete ribs; and
    wherein customizing or creating the patient interface device includes at least one of selecting the number of discrete ribs based on the determined hardness value and selecting dimensions of the discrete ribs based on the determined hardness value.

11. A method for determining an optimal hardness of a patient interface device, the method comprising:
    receiving a 3-D model of the patient interface device;
    receiving a 3-D model of a patient's face;
    determining a fit score between the patient interface device and the patient's face based on the 3-D model of the patient interface device and the 3-D model of the patient's face;
    determining a hardness value of the patient interface device based on the determined fit score;
    customizing a patient interface device based on the determined hardness value or creating a patient interface device based on the determined hardness value,
    wherein the patient interface device includes a continuous rib structure having varying heights and thicknesses;
    wherein customizing or creating the patient interface device includes selecting the heights and/or thicknesses of the rib structure based on the determined hardness value.

12. A method for determining an optimal hardness of a patient interface device, the method comprising:
    receiving a 3-D model of the patient interface device;
    receiving a 3-D model of a patient's face;
    determining a fit score between the patient interface device and the patient's face based on the 3-D model of the patient interface device and the 3-D model of the patient's face;
    determining a hardness value of the patient interface device based on the determined fit score; and customizing a patient interface device based on the determined hardness value or creating a patient interface device based on the determined hardness value, wherein the patient interface device includes a plurality of filled portions; wherein determining the fit score includes determining a plurality of fit scores, each fit score corresponding to one of the filled portions;

wherein determining the hardness includes determining a plurality of hardness values based on the determined plurality of fit scores, each hardness value corresponding to one of the filled portions; and wherein customizing or creating the patient interface device includes selecting materials for each of the filled portions based on the plurality of determined hardness values.

* * * * *